US010909680B2

(12) United States Patent
Ross et al.

(10) Patent No.: US 10,909,680 B2
(45) Date of Patent: Feb. 2, 2021

(54) METHOD AND SYSTEM FOR ASSESSING BURN WOUND DEPTH

(71) Applicant: MED-COMPLIANCE IQ, INC., Powell, OH (US)

(72) Inventors: Gary J. Ross, Powell, OH (US); Nathan Romano, Pickerington, OH (US); Eric Richardson, Pickerington, OH (US)

(73) Assignee: MED-COMPLIANCE IQ, INC., Powell, OH (US)

( * ) Notice: Subject to any disclaimer, the term of this patent is extended or adjusted under 35 U.S.C. 154(b) by 28 days.

(21) Appl. No.: 16/058,304

(22) Filed: Aug. 8, 2018

(65) Prior Publication Data

US 2019/0050991 A1 Feb. 14, 2019

Related U.S. Application Data

(60) Provisional application No. 62/542,610, filed on Aug. 8, 2017.

(51) Int. Cl.
| | |
|---|---|
| *G06T 7/00* | (2017.01) |
| *G16H 50/20* | (2018.01) |
| *G06T 7/55* | (2017.01) |
| *G16H 30/40* | (2018.01) |
| *G06N 3/00* | (2006.01) |
| *G06K 9/62* | (2006.01) |
| *G16H 40/67* | (2018.01) |

(52) U.S. Cl.
CPC .......... *G06T 7/0014* (2013.01); *G06K 9/6274* (2013.01); *G06K 9/6276* (2013.01); *G06K 9/6277* (2013.01); *G06N 3/00* (2013.01); *G06T 7/55* (2017.01); *G16H 30/40* (2018.01); *G16H 40/67* (2018.01); *G16H 50/20* (2018.01); *G06T 2207/10016* (2013.01); *G06T 2207/10132* (2013.01); *G06T 2207/20076* (2013.01); *G06T 2207/20084* (2013.01); *G06T 2207/30088* (2013.01); *G06T 2207/30096* (2013.01)

(58) Field of Classification Search
CPC ..... G06T 7/0014; G06T 7/55; G06T 2207/10016; G16H 50/20; G16H 30/40
See application file for complete search history.

(56) References Cited

U.S. PATENT DOCUMENTS

| | | | |
|---|---|---|---|
| 4,080,960 A | 3/1978 | Goans et al. | |
| 5,127,409 A | 7/1992 | Daigle | |
| 5,588,428 A | 12/1996 | Smith et al. | |
| 9,043,156 B2 | 5/2015 | Gallippi et al. | |
| 9,125,589 B2 | 9/2015 | Sørnes | |
| 9,643,030 B2 * | 5/2017 | Liu | A61B 8/485 |
| 9,990,472 B2 * | 6/2018 | Gurcan | G16H 50/20 |
| 10,083,508 B2 * | 9/2018 | Jiang | G06T 7/0016 |
| 2004/0039379 A1 | 2/2004 | Viator et al. | |
| 2004/0215075 A1 | 10/2004 | Zagzebski et al. | |
| 2017/0079530 A1 * | 3/2017 | DiMaio | A61B 5/0075 |
| 2017/0112472 A1 * | 4/2017 | Song | A61B 8/54 |
| 2018/0279943 A1 * | 10/2018 | Budman | G06F 19/321 |

OTHER PUBLICATIONS

Gnyawali et al., "High-Resolution Harmonics Ultrasound Imaging for Non-Invasive Characterization of Wound Healing in a Pre-Clinical Swine Model", PLOS One, 1 19, Mar. 23, 2015 (online).
Gennisson et al., "Ultrasound elastography: Principles and techniques", Diagnostic and Interventional Imaging, 94:487-495 (2013).
Franchi-Abella, "Ultrasound elastography: Advantages, limitations and artifacts of the different techniques from a study on a phantom", Diagnostic and Interventional Imaging, 94:497-501 (2013).
Budman et al, Design of a Smartphone Application for Automated Wound Measurements in Home Care, Connected Health Symposium 2015, www.iproc.org/2015/1/e16 (2015).

* cited by examiner

*Primary Examiner* — Santiago Garcia

(74) *Attorney, Agent, or Firm* — Porter Wright Morris & Arthur LLP

(57) ABSTRACT

A method for evaluating the depth of a burn wound in a subject comprises (a) receiving an imaging video of the burn wound collected by an ultrasound transducer, (b) evaluating nodes and edges connecting the nodes in a plurality of layers of the burn wound in a plurality of frames of the imaging video, with a classifier system, the classifier system comprising a convolutional neural network that compares the nodes and edges of the burn wound with nodes and edges in a plurality of layers of a plurality of historical burn wounds of known depth, and (c) assigning a depth to the burn wound, the assigned depth being an average of depths associated with a plurality of the historical burn wounds having a predetermined minimum similarity of nodes and edges to the nodes and edges of the burn wound.

14 Claims, No Drawings

METHOD AND SYSTEM FOR ASSESSING BURN WOUND DEPTH

RELATED APPLICATION

This application claims priority under 35 U.S.C. 119 of U.S. Application No. 62/542,610 filed Aug. 8, 2017, which is incorporated herein in its entirety.

FIELD OF THE INVENTION

The present invention is directed to methods and systems for assessing burn wound depth, and, in one embodiment, for distinguishing between a second degree, partial thickness burn and a third degree, full thickness burn. The methods and systems employ a classifier system comprising a convolutional neural network that compares the nodes and edges of the burn wound with nodes and edges of historical burn wounds of known depth.

BACKGROUND OF THE INVENTION

Up to 1.1 million Americans per year suffer from burn injuries that require medical care. The foundation of burn wound care is determining whether a patient has a deep burn, i.e., a third or fourth degree, full thickness burn, which requires excision and skin grafting for optimal healing, or a partial thickness burn, i.e., a first or second degree burn, that is expected to heal without surgery and without scarring. Accurate determination of burn wound depth is critical because over-estimation of a burn wound depth results in unnecessary surgery, unnecessary excision of viable skin and replacement with skin grafts that look different from surrounding skin. Skin grafts also typically lack the pliability and/or elasticity of undamaged skin and the ability to sweat for thermoregulation. On the other hand, underestimation of burn wound depth results in prolonged treatment, increased treatment costs, increased scarring, disfigurement and/or loss of function.

Clinical assessment, i.e., visual assessment by a physician, is most commonly used to determine burn wound depth. However, visual assessment is not very reliable, and even with the most experienced surgeons, clinical assessment is only accurate about 75% of the time when distinguishing between second degree and third degree burns. Accuracy decreases to about 50% for inexperienced surgeons. Burn injury depth is dynamic, especially in the first 24-48 hours post-burn injury, depending on the effectiveness of burn resuscitation or development of infection, which adds to the complexity of properly determining burn wound depth.

A variety of imaging modalities have been used for estimating burn wound depth. The current gold standard is laser Doppler imaging (LDI), that correlates blood flow with burn wound depth. However, LDI has not been widely adopted in at least the United States for various reasons, including, but not limited to, the difficulty of accurately interpreting the images and multiple variables that interfere with light-based detection of blood flow including, for example, residual pigments from silver dressings or tattoos, and patient conditions that affect blood flow such as infection, edema and use of vasoactive medicines.

Accordingly, a need exists for improved methods and systems for accurately assessing burn wound depth in order to select the most appropriate treatment.

SUMMARY OF THE INVENTION

It is therefore an object of the invention to provide improved methods and systems for accurately assessing burn wound depth.

In one embodiment, the invention is directed to a method for evaluating the depth of a burn wound in a subject. The method comprises (a) receiving an imaging video of the burn wound collected by an ultrasound transducer, (b) evaluating nodes and edges connecting the nodes in a plurality of layers of the burn wound in a plurality of frames of the imaging video, with a classifier system, the classifier system comprising a convolutional neural network that compares the nodes and edges of the burn wound with nodes and edges in a plurality of layers of a plurality of historical burn wounds of known depth, and (c) assigning a depth to the burn wound, the assigned depth being an average of depths associated with a plurality of the historical burn wounds having a predetermined minimum similarity of nodes and edges to the nodes and edges of the burn wound.

In another embodiment, the invention is directed to a system for evaluating the depth of a burn wound in a subject. The system comprises (a) an interface for receiving an imaging video of the burn wound, (b) a database comprising data of nodes and edges connecting the nodes in a plurality of layers of a plurality of historical burn wounds of known depth,(c) a classifier system operable to evaluate nodes and edges connecting the nodes in a plurality of layers of the burn wound in a plurality of frames of the imaging video, the classifier system comprising a convolutional neural network that compares the nodes and edges of the burn wound with nodes and edges of the plurality of historical burn wounds of known depth in the database, and operable to assign a depth to the burn wound, the assigned depth being an average of the depths associated with a plurality of the historical burn wounds having a predetermined minimum similarity of nodes and edges to the nodes and edges of the burn wound, and (d) an interface for communicating the assigned depth of the burn wound to a user.

The methods and systems of the invention are advantageous in providing improved assessment of burn wound depth, and particularly for distinguishing between second and third degree burns, and thereby allowing improved treatment decisions to be made, for example, avoiding unnecessary surgical treatment of second degree burns and ensuring appropriate treatment of third degree wounds. Burn wound treatment outcomes are therefore improved by the present methods and systems.

Additional objects and advantages of the invention will be fully apparent in view of the following detailed description.

DETAILED DESCRIPTION

The present methods and systems employ a classifier system comprising a convolutional neural network which evaluates nodes and edges connecting the nodes in a plurality of layers of the burn wound in a plurality of frames of an imaging video of the burn wound. The convolutional neural network of the classifier system compares the nodes and edges of the burn wound with nodes and edges in a plurality of layers of a plurality of historical burn wounds of known depth. Thus, the classifier system includes or is operable to access a database comprising data of nodes and edges connecting the nodes in a plurality of layers of the plurality of historical burn wounds.

The imaging video which is evaluated by the classifier system is collected by an ultrasound transducer. Burn injury denatures proteins and ultrasound allows detection of changes in the elastic property of the subcutaneous tissue beneath the skin surface. Using sound waves to detect tissue changes avoids the limitations of light based imaging technologies such as LDI. In one embodiment, the ultrasound transducer is a tissue Doppler elastography transducer. Tissue Doppler elastography imaging (TDI) detects changes in the elastic property of the subcutaneous tissue beneath the skin surface. Thus, TDI detects a specific physical change in the subcutaneous tissue in response to burn injury. Those changes can be detected/represented by changes in color (red=soft, blue=hard) in the image. Although ultrasound images such as TDI images are difficult to interpret without significant experience using the technology, the present methods and systems overcome this difficulty by employing the classifier system which uses machine learning software, i.e., a convolutional neural network, to assess burn wound depth, optionally with an indication of the probability that the burn is of partial thickness (second degree burn) or full thickness (third degree burn). Changes in tissue elasticity are converted to a quantitative value based on changes in the color pixels. Ultrasound imaging detects echoes of reflected ultrasound waves generated by the transducer applied to the skin. Standard B-mode/diagnostic ultrasound imaging may have noise artifacts from undesirable echoes from tissue interfaces that appear as bright white lines. Using sound waves in the harmonic range for tissues reduces image artifact and remarkably improves quality.

In a specific embodiment, the transducer is an accessory to a smart phone. In additional embodiments, a single scan using a linear array probe (3-18 MHz frequency range) on a Noblus ultrasound device obtains B-mode ultrasound, TDI elastography and color Doppler imaging (CDI). If TDI image analysis is unreliable, B-mode ultrasound is analyzed or Doppler flow imaging of blood vessels supplying the burn injury site is gated, and blood flow dynamics of gated region may be quantified.

The classifier system evaluates nodes and edges connecting the nodes in a plurality of layers of the burn wound in a plurality of frames of the imaging video and specifically comprises a convolutional neural network that compares the nodes and edges of the burn wound with nodes and edges in a plurality of layers of a plurality of historical burn wounds of known depth. As the number of the plurality of historical burn wounds of known depth in the classifier system is increased, the predictive capabilities of the methods and systems become more accurate. In specific embodiments, the plurality of historical burn wounds is at least 5, at least 10, at least 20, at least 30, at least 50, or at least 100. The classifier employs one or more image analysis algorithms to compare the nodes and edges of the burn wound with nodes and edges in a plurality of layers of historical burn wounds.

The historical burn wounds may be porcine burn wounds and/or human burn wounds. Porcine is a preferred preclinical model because it is widely accepted that porcine skin wound healing most closely resembles the human healing process. Anatomically, porcine skin shows high analogy to human skin. A review of twenty-five wound therapies revealed that porcine studies were in agreement with human studies 78% of the time, compared to 53% and 57% with rodent and in vitro models, respectively. With respect to translational value, the Wound Healing Society recommends the porcine model as the most relevant pre-clinical model of skin wound healing. The historical burn wounds are burn wounds of known depth and include multiple historical second degree burn wounds and multiple historical second degree burn wounds. In further embodiments, the historical burn wounds also include first degree burn wounds and fourth degree burn wounds.

The classifier system accurately predicts a burn wound as partial or full thickness from the data in the imaging video. The classifier system comprises the convolutional artificial neural network, essentially evaluating a graph of nodes and edges. The nodes are connected to each other through a set of edges. How connected or how disconnected a node is from one or another is determined by the weight of the edge. The artificial neural network evaluates a plurality of layers of the wound. Each node in each layer accepts input from its edges. The incoming signal is scaled up or down by the edge's weights. The sum of all the inputs is calculated by an activation function or rectifier for that layer in each node. If the node is active, it will output a signal to each of its output edges (which become the input edges of the next layer). The convolutional neural network is a bioinspired neural network based on the organization of an animal's visual cortex. Neurons are grouped to represent different areas of the view space or receptive fields within the visual cortex. The classifier is comprised of several layers. Each layer serves a purpose in the overall classification of features and ultimately the object or objects within an image. The high-level architecture of the artificial neural network comprises: 1. a first convolution layer with a rectified linear activation function; 2. a first max pooling layer; 3. a first local response normalization layer; 4. a second convolution layer with a rectified linear activation function; 5. a second max pooling layer; 6. a second local response normalization layer; 7. a first fully connected layer; 8. a second fully connected layer; and 9. a soft-max linear layer.

The classifier assigns a depth to the burn wound, the assigned depth being an average of depths associated with a plurality of the historical burn wounds having a predetermined minimum similarity of nodes and edges to the nodes and edges of the burn wound. The predetermined minimum may be quantified as similarity to a percentage of the nodes and edges of the burn wound which is the subject of the assessment. In specific embodiments, the plurality of historical burn wounds having a predetermined minimum similarity of nodes and edges to the nodes and edges of the burn wound subject to assessment have similarity to at least 50%, at least 60%, at least 70%, at least 80%, at least 90% or at least 95% of the nodes and edges of the burn wound subject to assessment. Similarity is defined by the classifier and, in specific embodiments, may be quantified as less than or equal to a maximum deviation in one or more node characteristics, for example, size, and optionally, one or more edge characteristics. In further specific embodiments, similarity is quantified as less than or equal to 20%, 15%, 10%, 5%, 4%, 3%, 2%, 1% or less deviation in one or more node characteristics, for example, size, and optionally, one or more edge characteristics.

In one embodiment, a probability percentage is associated with the assigned depth. The probability percentage is determined by the classifier system and in one embodiment is based on the number of nodes and edges of the burn wound to which the plurality of the historical burn wounds exhibit the predetermined minimum similarity of nodes and edges, relative to the total number of nodes and edges in the burn wound.

The methods as described may be performed locally to the burn patient or remotely from the patient. For remote performance, the imaging video may be received via the internet, and, in a specific embodiment, may be received from a remote server accessed via the internet. Thus, the methods and systems may use known web-based technologies, for example following a standard three-tiered architecture that is common practice in the information and technology industry comprising presentation (web), application programing interface (API), and a data tier. A photo of the exterior of the wound may also be provided, along with the ultrasound-derived imaging video, and other subject information. The wound observation may be captured through a web-based interface and saved into a database. The burn wound thickness assigned by the classifier system, for example either partial or full, and optionally the confidence score in the form of a percentage of probability, can be communicated directly to an attending physician or sent to the remote server accessed by an attending physician via the internet. A date to observe the patient's wound in the future may also be provided in the method and system.

While the present invention has been illustrated by the description of embodiments thereof, and while the embodiments have been described in considerable detail, it is not the intention of the Applicant to restrict or in any way limit the scope of the appended claims to such detail. Additional advantages and modifications will readily appear to those skilled in the art. Therefore, the application, in its broader aspects, is not limited to the specific details and illustrative examples shown and described. Accordingly, departures may be made from such details without departing from the spirit or scope of the general inventive concept.

What is claimed is:

1. A method for evaluating the depth of a burn wound in a subject, the method comprising
    (a) receiving an imaging video of the burn wound collected by an ultrasound transducer,
    (b) evaluating nodes and edges connecting the nodes in a plurality of layers of the burn wound in a plurality of frames of the imaging video, with a classifier system, the classifier system comprising a convolutional neural network that compares the nodes and edges of the burn wound with nodes and edges in a plurality of layers of a plurality of historical burn wounds of known depth, and
    (c) assigning a depth to the burn wound, the assigned depth being an average of depths associated with a plurality of the historical burn wounds having a predetermined minimum similarity of nodes and edges to the nodes and edges of the burn wound,
    wherein a probability percentage is associated with the assigned depth, and the probability percentage is the number of nodes and edges of the burn wound to which the plurality of the historical burn wounds exhibit the predetermined minimum similarity of nodes and edges, relative to the total number of nodes and edges in the burn wound.

2. A method for evaluating the depth of a burn wound in a subject, the method comprising
    (a) receiving an imaging video of the burn wound collected by an ultrasound transducer, wherein the transducer is a tissue Doppler elastography transducer,
    (b) evaluating nodes and edges connecting the nodes in a plurality of layers of the burn wound in a plurality of frames of the imaging video, with a classifier system, the classifier system comprising a convolutional neural network that compares the nodes and edges of the burn wound with nodes and edges in a plurality of layers of a plurality of historical burn wounds of known depth, and
    (c) assigning a depth to the burn wound, the assigned depth being an average of depths associated with a plurality of the historical burn wounds having a predetermined minimum similarity of nodes and edges to the nodes and edges of the burn wound,
    wherein a probability percentage is associated with the assigned depth, and the probability percentage is the number of nodes and edges of the burn wound to which the plurality of the historical burn wounds exhibit the predetermined minimum similarity of nodes and edges, relative to the total number of nodes and edges in the burn wound.

3. The method of claim 1, wherein the transducer is an accessory of a smart phone.

4. The method of claim 1, wherein the assigned depth is either a second degree, partial thickness burn wound or a third degree, full thickness burn wound.

5. The method of claim 1, wherein the assigned depth is communicated to a provider of the imaging video.

6. The method of claim 1, wherein the imaging video is received from a remote server accessed via the internet.

7. A system for evaluating the depth of a burn wound in a subject, the system comprising
    (a) an interface for receiving an imaging video of the burn wound,
    (b) a database comprising data of nodes and edges connecting the nodes in a plurality of layers of a plurality of historical burn wounds of known depth,
    (c) a classifier system operable to evaluate nodes and edges connecting the nodes in a plurality of layers of the burn wound in a plurality of frames of the imaging video, the classifier system comprising a convolutional neural network that compares the nodes and edges of the burn wound with nodes and edges of the plurality of historical burn wounds of known depth in the database, and operable to assign a depth to the burn wound, the assigned depth being an average of the depths associated with a plurality of the historical burn wounds having a predetermined minimum similarity of nodes and edges to the nodes and edges of the burn wound, and a probability percentage associated with the assigned depth, wherein the probability percentage is the number of nodes and edges of the burn wound to which the plurality of the historical burn wounds exhibit the predetermined minimum similarity of nodes and edges, relative to the total number of nodes and edges in the burn wound, and
    (d) an interface for communicating the assigned depth of the burn wound and probability percentage to a user.

8. The system of claim 7, wherein the assigned depth is either a second degree, partial thickness burn wound or a third degree, full thickness burn wound.

9. The system of claim 7, wherein the interface for communicating the assigned depth of the burn wound is operable to communicate the assigned depth to a provider of the imaging video.

10. The system of claim 7, wherein the interface for receiving an imaging video is operable to receive the imaging video from a remote server accessed via the internet.

11. The method of claim 2, wherein the transducer is an accessory of a smart phone.

12. The method of claim 2, wherein the assigned depth is either a second degree, partial thickness burn wound or a third degree, full thickness burn wound.

13. The method of claim 2, wherein the assigned depth is communicated to a provider of the imaging video.

14. The method of claim 2, wherein the imaging video is received from a remote server accessed via the internet.

\* \* \* \* \*

UNITED STATES PATENT AND TRADEMARK OFFICE
CERTIFICATE OF CORRECTION

Page 1 of 1

PATENT NO. : 10,909,680 B2
APPLICATION NO. : 16/058304
DATED : February 2, 2021
INVENTOR(S) : Gary J. Ross et al.

It is certified that error appears in the above-identified patent and that said Letters Patent is hereby corrected as shown below:

In the Claims

Claim 7, Column 6, Line 21, change "bum" to --burn--.

Claim 7, Column 6, Line 33, change "bum" to --burn--.

Claim 7, Column 6, Line 40, change "bum" to --burn--.

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*